United States Patent [19]

Shepherd

[11] 4,383,904
[45] May 17, 1983

[54] PHOTOCHEMICAL EPOXIDATION

[75] Inventor: James P. Shepherd, Union, N.J.

[73] Assignee: Celanese Corporation, New York, N.Y.

[21] Appl. No.: 304,435

[22] Filed: Sep. 21, 1981

[51] Int. Cl.$^3$ .............................................. C07C 3/24
[52] U.S. Cl. .................................................. 204/162 R
[58] Field of Search ..................... 204/162 R; 549/532

[56] References Cited

U.S. PATENT DOCUMENTS 4,345,984 8/1982 Mihelich ......................... 204/162 R

FOREIGN PATENT DOCUMENTS 55-9004 1/1980 Japan ............................... 204/162 R
820461 9/1959 United Kingdom ............ 204/162 R Primary Examiner—Leland A. Sebastian
Attorney, Agent, or Firm—Depaoli & O'Brien

[57] ABSTRACT

This invention provides a process for photochemical epoxidation of olefins with molecular oxygen in a liquid phase with irradiation in the presence of a combination of 1,2-diketone photosensitizers.

Propylene can be converted to propylene oxide by reaction with molecular oxygen in an ortho-dichlorobenzene reaction medium in the presence of 2,3-butanedione and 1-phenyl-1,2-propanedione photosensitizers, at a space time yield rate of at least 15 grams per liter hour.

12 Claims, No Drawings

PHOTOCHEMICAL EPOXIDATION

BACKGROUND OF THE INVENTION

Epoxides are important chemical commodities which are employed as starting materials for the preparation of antifreeze compositions, humectants, pharmaceutical preparations, cosmetic formulations, as monomers for the preparation of polymers, and the like.

Epoxides such as ethylene oxide and propylene oxide currently are prepared by a vapor phase catalytic method and by the two-step chlorohydrin route, respectively. The vapor phase process in industrial production of epoxides is confined to the preparation of ethylene oxide. Higher olefins are not amenable to a vapor phase catalytic process to provide economic production of the corresponding epoxide.

The older chlorohydrin route is the principal industrial process which supplies the largest quantities of propylene oxide for commerce. This process is suitable for conversion of ethylene and propylene to their corresponding epoxides, but higher olefins are not particularly adaptable to the chlorohydrin route.

Another process for preparation of epoxides is that involving organic peroxide or hydroperoxide oxidation of olefins. This process appears to have wider application insofar as olefin structure is concerned than do the first two methods described. Highly substituted ethylenes such as tetramethylethylene and trimethylethylene react smoothly and rapidly with a peroxy compound to give the corresponding epoxides. However, ethylenic compounds having much lower degrees of substitution about the carbon to carbon double bond (e.g., ethylene and propylene) react sluggishly with peroxy compounds and the rate of formation of the corresponding epoxides is very slow.

Each of the above described processes has inherent disadvantages. For example, vapor phase catalytic oxidation of ethylene to ethylene oxide requires large volume equipment and the handling of large quantities of potentially explosive mixtures of ethylene and oxygen. The chlorohydrin route to propylene oxide essentially involves a two-step process and in addition, chlorinated byproducts are produced. The process involving hydroperoxide oxidation of olefins is potentially hazardous if relatively large quantities of peroxy compound are to be handled.

Other prior art processes which are more pertinent for purposes of the present invention involve liquid phase olefin epoxidation with molecular oxygen. These prior art processes propose a variety of approaches to an improved balance of reaction variables such as specific oxidation catalysts or catalyst-solvent systems, the presence of polymerization inhibitors, the use of neutralizing agents such as metal hydroxides, the control of oxygen pressure, and the like. These prior art processes are disclosed in U.S. Patents which include U.S. Pat. Nos. 2,279,470; 2,366,724; 2,530,509; 2,650,927; 2,741,623; 2,780,634; 2,780,635; 2,837,424; 2,838,524; 2,879,276; 2,942,007; 2,974,161; 2,977,374; 2,985,668; 3,153,058; 3,210,380; 3,228,967; 3,228,968; 3,232,957; 3,238,229; 3,275,662; 3,281,433; 3,428,658; 3,674,813; 3,980,676; and references cited therein.

Among the more recent developments are liquid phase reactions in which olefins are converted to epoxides by a photooxidation mechanism. For example, Japanese Pat. No. 80/09,004 [C.A. 92, 164507 (1980)] describes the epoxidation of propylene with oxygen in a polar solvent in the presence of sulfur dioxide under irradiation with light of at least 2600 angstroms wavelength.

In J. Am. Chem. Soc., 98(14), 4193 (1976), N. Shimizu and P. D. Bartlett report the results of photooxidation of olefins sensitized by α-diketones and by benzophenone. Epoxides are produced, as well as allylic hydroperoxides and oxetanes.

There is continuing effort to develop improved and more efficient processes for the production of epoxides from olefins.

Accordingly, it is a main object of this invention to provide an improved liquid phase process for converting olefins to epoxides with molecular oxygen.

It is another object of this invention to provide a photochemical process for efficient epoxidation of olefins in liquid phase with molecular oxygen.

It is a further object of this invention to provide a liquid phase photochemical process for converting propylene to propylene oxide with molecular oxygen at a space time yield (STY) rate of at least 15 grams per liter hour.

Other objects and advantages of the present invention shall become apparent from the accompanying description and examples.

DESCRIPTION OF THE INVENTION

One or more objects of the present invention are accomplished by the provision of a process for the photochemical epoxidation of olefins which comprises oxidizing an alkene compound with molecular oxygen in liquid phase with irradiation in the presence of at least two 1,2-diketone photosensitizers which absorb light in a range between about 3700–4600 angstroms.

The term "alkene" is meant to include acyclic and cyclic alkenes. Illustrative of suitable alkenes are those containing between about 3–12 carbon atoms such as propylene, 2-methylpropene, butene, 1,3-butadiene, pentene, hexene, heptene, decene, cyclopentene, cyclohexene, 4-methylhexene, cycloheptene, norbornene, and the like. The alkene can be a constituent contained in a light hydrocarbon stream from a petroleum refinery cracking operation.

The term "1,2-diketone" as employed herein refers to 1,2-diketone photosensitizer compounds in which the two vicinal carbonyl groups are freely rotatable around the connective bond with respect to each other. Excluded from the definition are 1,2-diketone compounds such as 9,10-phenanthrene quinone and ortho-chloranil. Included in the definition are 1,2-diketone photosensitizers which have freely rotatable ketone groups and which absorb electromagnetic radiation in the wavelength range between about 3700–4600 angstroms, such as 2,3-butanedione (biacetyl), 1-phenyl-1,2-propanedione, benzil, 4,4'-dimethoxybenzil, 4,4'-dimethylbenzil, 4,4'-dichlorobenzil, 1,4-dibromo-2,3-butanedione, 4-nitrobenzil, 1,3-bis(phenylglyoxylyl)benzene, 1,4-bis(phenylglyoxylyl)benzene, 4,4'-dibenzilylether, 4,4'-dibenzilylsulfone, and the like.

The molecular oxygen which is employed can be either in pure form or present as a component of a gasiform stream such as air.

The invention can be conducted either batchwise or continuously in equipment which provides adequate exposure of the liquid reaction medium to an electromagnetic radiation source. Either glassware is employed, or alternatively metal equipment is used which has transparent sections or ports.

The control of the temperature and other reaction conditions of the exothermic reaction are facilitated when the liquid phase in the reaction zone comprises the alkene and molecular oxygen reactants dissolved in an aprotic solvent. The preferred solvent is one that is oxidatively stable and not susceptible to an environment of free radicals initiated by electromagnetic radiation input.

Alkyl substituted aromatic hydrocarbons such as toluene and xylene are not desirable solvents for the practice of the invention process, since they are sensitive to free radical attack and tend to form phenolic and quinonoid type of byproducts in the presence of molecular oxygen.

Illustrative of oxidatively stable solvents are acetonitrile, tetrahydrofuran, dimethylformamide, 1,2,4-trichlorobenzene, o-dichlorobenzene, monochlorobenzene, benzene, carbon tetrachloride, 1,1,2-trichlorofluoroethane, ethyl acetate, ethyleneglycol diacetate, cyclohexane, and the like.

The choice of solvent medium appears to affect the overall rate of alkene conversion and selectivity to the desired epoxide product. Superior results are obtained with acetonitrile or o-dichlorobenzene as the solvent medium. It is preferred that the solvent constitute at least 50 percent by volume of the liquid phase.

The electromagnetic radiation can be supplied by any conventional type of lamp which has an emission spectrum that includes a 3700-4600 angstroms wavelength range, e.g., an Hanovia 450 W medium-pressure mercury lamp. It is preferred to exclude ultraviolet light below about 3700 angstroms from the epoxidation reaction zone, since the higher energy radiation tends to cause cleavage and loss of 1,2-diketone photosensitizers. Light filters can be employed as necessary to restrict the radiation to the desired 3700-4600 angstroms wavelength range. If the radiation is being transmitted through a Pyrex glass reactor vessel, the Pyrex glass filters out most of the undesirable ultraviolet wavelength radiation.

In the practice of the process, the liquid phase reaction medium is maintained at a temperature in the range between about −10° C. and 150° C., and preferably in the range between about 10°–50° C.

The pressure in the reaction system can be varied in the range between about 15-1500 psi, and preferably in the range between about 90-200 psi. In the case of a normally gaseous alkene such as propylene, it is highly advantageous to provide a sufficiently high pressure at a given reaction zone temperature to cause the said gaseous alkene to be at least partially liquefied during the course of the epoxidation reaction. A higher pressure increases the dissolution of both alkene and molecular oxygen in a liquid phase solvent medium, and promotes the efficiency of the epoxidation reaction.

The molecular oxygen is consumed at a rapid rate under the epoxidation conditions. Hence, the amount of molecular oxygen is fed into the reaction system in a quantity that does not permit the formation of potentially hazardous explosive mixtures of molecular oxygen and organic materials. Further, conducting the epoxidation reaction under oxygen-starved conditions serves to prevent degradation of the epoxide product which is produced.

The rate of alkene conversion and the selectivity to epoxide product are increased when the photosensitizer component in the reaction system consists of at least two 1,2-diketones. Unexpectedly it has been found that the efficiency of the epoxidation reaction is increased when two or more 1,2-diketone photosensitizers are employed rather than the equivalent quantity of only one 1,2-diketone compound.

The said combination of two or more 1,2-diketone photosensitizers usually is employed in a quantity between about 0.1-40 weight percent, based on the weight of alkene reactant which is present in the liquid phase reaction zone. As between any two 1,2-diketone photosensitizers being employed, the said photosensitizers can be present in a weight ratio between about 1-10-:1-10 relative to each other.

Under optimum conditions, an alkene such as propylene in a solvent medium such as o-dichlorobenzene, and in the presence of a photosensitizer combination such as 1-phenyl-1,2-propanedione/biacetyl (3.5:1), can be converted to propylene oxide at a space time yield rate of at least 15 grams per liter hour. A lower rate is obtained if only one 1,2-diketone photosensitizer is employed, or if a 1,2-diketone photosensitizer is employed which is not freely rotatable about around the 1,2-diketone connecting bond, e.g., ortho-chloranil.

In the practice of the process the intimate contact between the alkene and molecular oxygen reactants in the liquid phase medium is established by stirring, sparging, shaking, spraying or other such means of vigorous agitation. The agitation of the reaction medium also facilitates removal of heat of reaction to heat exchangers.

The admixture and contact of the reactants can be accomplished in several ways. For example, the alkene and molecular oxygen can be premixed with a solvent and introduced into the reaction zone; or the reaction zone may be charged with solvent, and the alkene and molecular oxygen introduced simultaneously through separate feed lines.

In one embodiment, a mixture of alkene and molecular oxygen is added to a solvent solution of 1,2-diketone photosensitizers in a continuously strired reactor under selected conditions of temperature and pressure. The oxygen input is controlled at a rate which keeps the oxygen concentration in the off-gas at less than about one percent.

After completion of the epoxidation reaction (e.g., after a reaction period of about 1-5 hours), in a batch type operation the entire reaction product mixture is removed from the reactor system, and then conventional techniques such as distillation are employed for separation of the epoxide product, and recycle of recovered fractions such as alkene and solvent.

In a continuous type operation, the gaseous and liquid effluent is continuously withdrawn from the reaction zone and subjected to extraction and/or distillation and the like means to separate and recover the epoxide product, solvent, unreacted alkene and oxidation byproducts.

An important advantage of the invention process is the high selectivity of the epoxidation reaction over a broad range of processing conditions. A propylene conversion to propylene oxide with a selectivity in the range of about 90-100 percent is readily achieved.

The following examples are further illustrative of the present invention. The reactants and other specific ingredients are presented as being typical, and various modifications can be derived in view of the foregoing disclosure within the scope of the invention.

Examples I–IV demonstrate typical results obtained when propylene was epoxidized in the presence of one 1,2-diketone and the results obtained in the presence of two 1,2-diketones. In Example IV the propylene oxide was produced at the rate of 6.7 mmole per hour.

Examples V–IX demonstrate a comparison of propylene epoxidation reactions involving a 2:1 molar ratio of 1-phenyl-1,2-propanedione/biacetyl mixture with reactions involving equal quantities of the individual photosensitizers. The results obtained are summarized in Table I.

Example X, when compared to Examples VII and IX, demonstrates the increased propylene oxide rate of formation which is obtained when a combination of two photosensitizers is employed in a quantity which is substantially the molar equivalent of either photosensitizer employed individually.

Examples XI-XIV demonstrate the effect of high propylene concentration and elevated pressure on the relative epoxidation rate during propylene conversion. The results obtained are summarized in Table II.

It was observed that the rate of epoxidation is dependent both on the particular ratio of the 1,2-diketone photosensitizers employed and on the total concentration of the photosensitizer mixture.

It was also found that the quantum efficiency of epoxidation under pressure conditions is at least about 75 percent of the available absorbable light efficiency. The quantum energy increases proportionally as the pressure increases.

EXAMPLE I

A solution of 2.75 grams of biacetyl (0.13M) in 250 milliliters of o-dichlorobenzene was placed in a cylindrical photochemical reactor equipped with a water-cooled Pyrex lamp immersion well and a Dry Ice condenser. The path length through the annular reaction space was 0.5 cm. The system was purged with oxygen introduced through a fritted glass disc in the bottom of the reactor. The solution was saturated with propylene (approx. 0.1 mole), introduced through the same fritted glass disc.

The oxygen sparge was reestablished and the solution was irradiated with a 450 Watt high pressure mercury lamp for 180 minutes. The reaction temperature was maintained at 15°–25° C. with the water-cooled immersion well and the return of condensed propylene from the Dry ice condenser. Analysis of the reaction mixture by gas chromatography indicated the formation of 15 mmoles of propylene oxide (5 mmoles/hr.) and 1.0 mmole of acetone (sensitizer decomposition product).

EXAMPLE II

A solution of 4.5 grams of benzil (0.086M) in 250 milliliters of o-dichlorobenzene was placed in the apparatus described in Example I. The system was purged with oxygen and saturated with propylene, then irradiated (450 Watt high pressure mercury lamp) with oxygen sparging for 120 minutes. Irradiation under these conditions produced 7.0 mmoles of propylene oxide (3.5 mmoles/hr.) as the only product.

EXAMPLE III

A solution of 3.5 grams of 1-phenyl-1,2-propanedione (0.095M) in 250 milliliters of o-dichlorobenzene was charged to the apparatus described in Example I. The system was purged with oxygen and saturated with propylene. Irradiation of the solution (1000 Watt tungsten lamp) with oxygen sparging for 250 minutes produced 19.0 mmoles of propylene oxide (4.6 mmoles/hr.) and 1.0 mmole of acetone.

EXAMPLE IV

A solution of 0.52 gram of biacetyl (0.024M) and 1.90 grams of 1-phenyl-1,2-propanedione (0.051M) in 250 milliliters of o-dichlorobenzene was charged to the apparatus described in Example I. The system was purged with oxygen and saturated with propylene. Irradiation of the solution (1000 Watt tungsten lamp) with oxygen sparging for 150 minutes produced 16.7 mmoles of propylene oxide (6.7 mmoles/hr.) and 0.7 mmole of acetone.

EXAMPLE V

A solution of 0.75 gram of biacetyl (0.035M) and 2.7 grams of 1-phenyl-1,2-propanedione (0.073M) in 250 milliliters of o-dichlorobenzene was charged to the apparatus described in Example I. The system was purged with oxygen and saturated with propylene. Irradiation (1000 Watt tungsten lamp) with oxygen sparging for 150 minutes produced 10.9 mmoles of propylene oxide (4.4 mmoles/hr.) and a trace amount of acetone.

EXAMPLE VI

A solution of 0.75 gram of biacetyl (0.035M) in 250 milliliters of o-dichlorobenzene was charged to the apparatus described in Example I. The system was purged with oxygen and saturated with propylene. Irradiation of this mixture (1000 Watt tungsten lamp) for 70 minutes while sparging with oxygen produced 2.0 mmoles of propylene oxide (1.7 mmoles/hr.) as the only detectable product.

EXAMPLE VII

A solution of 2.25 grams of biacetyl (0.104M) in 250 milliliters of o-dichlorobenzene was charged to the apparatus described in Example I. The system was purged with oxygen and saturated with propylene. Irradiation of this mixture (1000 Watt tungsten lamp) for 70 minutes with oxygen sparging produced 4.0 mmoles of propylene oxide (3.4 mmoles/hr.) as the only detectable product.

EXAMPLE VIII

A solution of 2.7 grams of 1-phenyl-1,2-propanedione (0.073M) in 250 milliliters of o-dichlorobenzene was charged to the apparatus described in Example I. The system was purged with oxygen and saturated with propylene. Irradiation (1000 Watt tungsten lamp) of the mixture with oxygen sparging for 70 minutes produced 2.8 mmoles of propylene oxide (2.4 mmoles/hr.) and a trace amount of acetone.

EXAMPLE IX

A solution of 4.05 grams of 1-phenyl-1,2-propanedione (0.109M) in 250 milliliters of o-dichlorobenzene was charged to the apparatus described in Example I. The system was purged with oxygen and saturated with propylene. Irradiation (1000 Watt tungsten lamp) of the mixture with oxygen sparging for 70 minutes produced 3.7 mmoles of propylene oxide (3.2 mmoles/hr.) and a trace amount of acetone.

EXAMPLE X

A solution of 1.12 grams biacetyl (0.052M) and 2.02 grams 1-phenyl-1,2-propanedione (0.054M) in 250 milliliters o-dichlorobenzene was charged to the apparatus described in Example I. The system was purged with oxygen, then saturated with propylene. Irradiation (1000 Watt tungsten lamp) of this mixture for 70 minutes with oxygen sparging produced 4.8 mmoles of propylene oxide (4.1 mmoles/hr.) as the only detectable product.

The quantities of biacetyl and 1-phenyl-1,2-propanedione employed were one-half the respective quantities used in Examples VII and IX. Propylene oxide formation rates in Examples VII and IX were 3.4 and 3.2 mmoles/hr., respectively. The rate of 4.1 mmoles/hr. observed in this Example demonstrated that propylene oxide formation rates may be increased by using a multiple sensitizer system in accordance with the present invention.

EXAMPLE XI

Pressurized reactions were conducted in a stirred pressure reactor consisting of a 750 milliliter glass bowl (¼" flint glass) bolted by a flange to a stainless steel cover. A solution of 0.5 gram of biacetyl (0.017M) and 1.8 grams of 1-phenyl-1,2-propanedione (0.035M) in 350 milliliters o-dichlorobenzene was placed in the reactor. The solution was saturated with propylene and the headspace of the reactor was purged with oxygen.

The reactor was sealed and irradiated for 120 minutes with an externally placed 450 Watt high pressure mercury lamp. The temperature was maintained at 15°–20° C. by a water flow through the reactor cooling coil. The pressure during the reaction was 15–20 psia. Analysis by gas chromatography indicated formation of 2.1 mmoles of propylene oxide (1.05 mmoles/hr.) as the only product.

EXAMPLE XII

A solution of 0.4 gram of biacetyl (0.012M) and 1.4 grams of 1-phenyl-1,2-propanedione (0.024M) in 300 milliliters o-dichlorobenzene was charged to the Example X pressure reactor. Condensed propylene (46.7 grams, 2.84M) was added, increasing the pressure of 70 psia. The pressure was increased to 98 psia with oxygen and the solution was vigorously stirred. Irradiation (450 Watt high pressure mercury lamp) for 90 minutes produced 9.3 mmoles of propylene oxide (6.2 mmoles/hr.) as the only product.

EXAMPLE XIII

A solution of 0.4 gram of biacetyl (0.014M) and 1.4 grams of 1-phenyl-1,2-propanedione (0.028M) in 250 milliliters of o-dichlorobenzene was charged to the pressure reactor. Condensed propylene (45.6 grams, 3.20M) was added increasing the pressure to 80 psia. Nitrogen was added to bring the pressure to 150 psia, and oxygen was added to a pressure of 169 psia. Irradiation (450 Watt high pressure mercury lamp) of the vigorously stirred solution for 90 minutes produced 11.2 mmoles of propylene oxide (7.5 mmoles/hr.) as the only product.

EXAMPLE XIV

Biacetyl (0.28 gram, 0.014M) and 1-phenyl-1,2-propanedione (1.0 gram, 0.029M) were charged to the pressure reactor. Condensed propylene (118.0 grams, 12.2M) was placed in the reactor, increasing the pressure to 144 psia. Nitrogen (21 psi) and oxygen (20 psi) were added to bring the pressure to 185 psia. Irradiation (450 Watt high pressure mercury lamp) for 90 minutes produced 3.05 mmoles of propylene oxide (2.0 mmoles/hr.) as well as 7.15 mmoles of acetaldehyde (4.7 mmoles/hr.) and a detectable quantity of formaldehyde.

TABLE I

Comparison of Propylene Oxide Formation Rates Using Single Sensitizer And Multiple Sensitizers

| Example | Biacetyl, M | 1-Phenyl-1,2-Propanedione, M | Total Sensitizer, M | Rate, mmoles PO/hr. |
|---|---|---|---|---|
| 5 | 0.035 | 0.073 | 0.108 | 4.4 |
| 6 | 0.035 | — | 0.035 | 1.7 |
| 7 | 0.104 | — | 0.104 | 3.4 |
| 8 | — | 0.073 | 0.073 | 2.4 |
| 9 | — | 0.109 | 0.109 | 3.2 |

TABLE II

Effect Of Propylene Concentration On Epoxidation Rate

| Example | Propylene, M | Atmosphere | Pressure, psia | Rel. Rate[a] |
|---|---|---|---|---|
| 11 | 0.38 | $O_2$ | 15–20 | 1.00 |
| 12 | 2.84 | $O_2$ | 98 | 5.90 |
| 13 | 3.20 | Air | 169 | 7.10 |
| 14 | 12.2[b] | 50% $N_2$, 50% $O_2$ | 185 | 1.90[c] |

[a]Rates relative to 1.05 mmoles PO/hr for saturated propylene (0.38M) at 1 atm.
[b]Condensed propylene.
[c]Selectivity to PO = 30%; acetaldehyde and formaldehyde also formed.

I claim:

1. A process for the photochemical epoxidation of olefins which comprises oxidizing an alkene compound with molecular oxygen in liquid phase with irradiation in the presence of at least two 1,2-diketone photosensitizers which absorb light in a range between about 3700–4600 angstroms.

2. A process in accordance with claim 1 wherein the alkene compound contains between about 3–12 carbon atoms.

3. A process in accordance with claim 1 wherein the alkene is propylene.

4. A process in accordance with claim 1 wherein the liquid phase comprises an aprotic solvent medium.

5. A process in accordance with claim 1 wherein the liquid phase comprises an o-dichlorobenzene solvent medium.

6. A process in accordance with claim 1 wherein the liquid phase comprises an acetonitrile solvent medium.

7. A process in accordance with claim 1 wherein the quantity of photosensitizers in the reaction medium is in the range between about 0.1–40 weight percent, based on the weight of alkene compound.

8. A process in accordance with claim 1 wherein the reaction medium contains two 1,2-diketone photosensitizers, and the said photosensitizers are present in a weight ratio between about 1–10:1–10.

9. A process in accordance with claim 1 wherein the photosensitizers in the reaction medium comprise 2,3-butanedione and 1-phenyl-1,2-propanedione.

10. A process in accordance with claim 1 wherein the photochemical epoxidation is conducted at a temperature in the range between about −10° C. and 150° C.

11. A process in accordance with claim 1 wherein the photochemical epoxidation is conducted at a pressure between about 15–1500 psi.

12. A process in accordance with claim 1 wherein the epoxide product is produced at a space time yield rate of at least 15 grams per liter hour.

* * * * *